(12) United States Patent
Crawford et al.

(10) Patent No.: US 7,497,847 B2
(45) Date of Patent: Mar. 3, 2009

(54) SAFETY SHIELD SYSTEM FOR A SYRINGE

(75) Inventors: Jamie Crawford, New York, NY (US); Frank Francavilla, Branchville, NJ (US); Roger Groskopf, Saddle Brook, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 170 days.

(21) Appl. No.: 10/699,971

(22) Filed: Nov. 3, 2003

(65) Prior Publication Data
US 2005/0096598 A1    May 5, 2005

(51) Int. Cl.
*A61M 5/32* (2006.01)
*A61M 5/00* (2006.01)

(52) U.S. Cl. .......... 604/198; 604/110; 604/192

(58) Field of Classification Search ......... 604/93.01, 604/110, 181, 187, 192–198, 125, 129, 158, 604/162, 164.08, 263; 128/919
See application file for complete search history.

(56) References Cited

U.S. PATENT DOCUMENTS

| | | | |
|---|---|---|---|
| 4,573,976 A | 3/1986 | Sampson | |
| 4,631,057 A | 12/1986 | Mitchell | |
| 4,737,144 A | 4/1988 | Choksi | |
| 4,747,831 A | 5/1988 | Kulli | |
| 4,795,432 A | 1/1989 | Karczmer | |
| 4,813,940 A | 3/1989 | Parry | |
| 4,932,940 A * | 6/1990 | Walker et al. ......... | 604/110 |
| 4,985,021 A | 1/1991 | Straw | |
| 4,998,920 A | 3/1991 | Johnson | |
| 5,026,356 A | 6/1991 | Smith | |
| 5,053,018 A | 10/1991 | Talonn | |
| 5,061,251 A | 10/1991 | Juhasz | |
| 5,151,088 A | 9/1992 | Allison | |
| 5,156,599 A | 10/1992 | Ranford | |
| 5,163,918 A | 11/1992 | Righi | |
| 5,193,552 A | 3/1993 | Columbus | |
| 5,197,953 A | 3/1993 | Colonna | |

(Continued)

FOREIGN PATENT DOCUMENTS

EP    0 307 367 A1    6/1992

(Continued)

*Primary Examiner*—Kevin C Sirmons
*Assistant Examiner*—Elizabeth R MacNeill
(74) *Attorney, Agent, or Firm*—David M. Fortunato; Cohen, Pontani, Lieberman & Pavane LLP

(57) ABSTRACT

A medical device includes a syringe assembly and a shield system for delivering medicament to a patient. The syringe assembly includes a barrel defining a medicament reservoir, a needle cannula coupled to the barrel and in fluid communication with the reservoir, a plunger having a stopper positioned in the reservoir and a thumb pad for moving the plunger in the reservoir. The shield system has a shield coupled to a forward end of the barrel, the shield being movable from a first position disposed from the needle cannula tip to a second position during insertion of the needle into a patient and movable from the second position to a third position covering the needle cannula tip after the needle cannula is removed from the patient. An urging member urges the shield to the third position upon removal of the needle cannula from the patient.

35 Claims, 8 Drawing Sheets

U.S. PATENT DOCUMENTS

| | | |
|---|---|---|
| 5,201,708 A | 4/1993 | Martin |
| 5,217,437 A | 6/1993 | Talonn |
| 5,242,420 A | 9/1993 | Martin |
| 5,246,427 A | 9/1993 | Sturman |
| 5,267,972 A | 12/1993 | Anderson |
| 5,295,965 A | 3/1994 | Wilmot |
| 5,300,040 A | 4/1994 | Martin |
| 5,304,149 A | 4/1994 | Morigi |
| 5,308,332 A | 5/1994 | Dillard, III |
| 5,312,372 A | 5/1994 | DeHarde et al. |
| 5,336,176 A | 8/1994 | Yoon |
| 5,342,309 A | 8/1994 | Hausser |
| 5,342,320 A | 8/1994 | Cameron |
| 5,370,628 A | 12/1994 | Allison |
| 5,385,555 A | 1/1995 | Hausser |
| 5,389,085 A * | 2/1995 | D'Alessio et al. ............ 604/198 |
| 5,417,660 A | 5/1995 | Martin |
| 5,429,612 A * | 7/1995 | Berthier ....................... 604/198 |
| 5,562,626 A | 10/1996 | Sanpietro |
| 5,573,513 A | 11/1996 | Wozencroft |
| 5,651,774 A | 7/1997 | Taranto |
| 5,658,254 A | 8/1997 | Reichenbach |
| 5,681,292 A | 10/1997 | Tober |
| 5,713,871 A | 2/1998 | Stock |
| 5,735,823 A | 4/1998 | Berger |
| 5,769,822 A | 6/1998 | McGary |
| 5,800,395 A | 9/1998 | Botich et al. |
| 5,800,403 A | 9/1998 | Pressly, Sr. et al. |
| 5,882,342 A | 3/1999 | Cooper |
| 6,017,329 A | 1/2000 | Hake |
| 6,077,253 A | 6/2000 | Cosme |
| 6,162,197 A | 12/2000 | Mohammad |
| 6,228,054 B1 | 5/2001 | Dysarz |
| 6,319,233 B1 | 11/2001 | Jansen |
| 6,432,087 B1 | 8/2002 | Hoeck et al. |
| 6,432,088 B1 | 8/2002 | Huang et al. |
| 6,440,104 B1 | 8/2002 | Newby et al. |
| 6,443,929 B1 | 9/2002 | Kuracina |
| 6,458,101 B1 | 10/2002 | Hu |
| 6,458,105 B1 | 10/2002 | Rippstein et al. |
| 6,461,333 B1 | 10/2002 | Frezza |
| 6,461,362 B1 | 10/2002 | Halseth |
| 6,475,194 B2 | 11/2002 | Domici, Jr. |
| 6,478,780 B1 | 11/2002 | Shields |
| 6,494,863 B1 | 12/2002 | Shaw |
| 6,511,460 B1 | 1/2003 | Arnissolle |
| 6,514,229 B1 | 2/2003 | Huang |
| 6,527,742 B1 | 3/2003 | Malenchek |
| 6,530,903 B2 | 3/2003 | Wang et al. |
| 6,547,762 B1 | 4/2003 | Botich et al. |
| 6,558,357 B1 | 5/2003 | Hoeck |
| 6,565,540 B1 | 5/2003 | Perouse |
| 6,569,115 B1 | 5/2003 | Barker |
| 6,569,124 B1 | 5/2003 | Perouse |
| 6,589,209 B1 | 7/2003 | Dysarz |
| 6,595,954 B1 | 7/2003 | Luther |
| 6,605,073 B1 | 8/2003 | Pressly, Sr. et al. |
| 6,884,237 B2 * | 4/2005 | Asbaghi ...................... 604/198 |
| 2002/0004648 A1 | 1/2002 | Larsen et al. |
| 2002/0065488 A1 | 5/2002 | Suzuki et al. |
| 2002/0193737 A1 | 12/2002 | Popovsky |
| 2002/0193746 A1 | 12/2002 | Chevallier |
| 2002/0193747 A1 | 12/2002 | Denolly |
| 2003/0023205 A1 | 1/2003 | Botich |
| 2003/0028171 A1 | 2/2003 | DeHarade |
| 2003/0036730 A1 | 2/2003 | Teichert |
| 2003/0050601 A1 | 3/2003 | Righi |
| 2003/0050607 A1 | 3/2003 | Gaagnieux |
| 2003/0078546 A1 | 4/2003 | Jensen |
| 2003/0083627 A1 | 5/2003 | Chen |
| 2003/0114799 A1 | 6/2003 | Cheikh |
| 2003/0144630 A1 | 7/2003 | Chang |
| 2003/0149403 A1 | 8/2003 | Barker |
| 2003/0149404 A1 | 8/2003 | Lehmann |

FOREIGN PATENT DOCUMENTS

| | | |
|---|---|---|
| EP | 0 680 767 A1 | 11/1995 |
| EP | 0 864 335 A2 | 9/1996 |
| EP | 0 740 942 A1 | 11/1996 |
| EP | 0 966 983 A1 | 12/1999 |
| EP | 1 258 263 A1 | 11/2002 |
| EP | 1 260 242 A1 | 11/2002 |
| EP | 0 901 391 B1 | 1/2003 |
| EP | 0 963 213 B1 | 1/2003 |
| EP | 1 273 316 A1 | 1/2003 |
| EP | 1 281 410 A1 | 2/2003 |
| EP | 0 916 354 B1 | 3/2003 |
| EP | 1 287 842 A1 | 3/2003 |
| EP | 1 291 029 A1 | 3/2003 |
| EP | 1 291 030 A1 | 3/2003 |
| EP | 1 317 938 A1 | 6/2003 |
| EP | 0 984 804 B1 | 7/2003 |
| EP | 1 329 234 A2 | 7/2003 |
| EP | 0 941 134 B1 | 8/2003 |
| EP | 1 205 173 A2 | 9/2003 |
| EP | 1 205 173 A3 | 9/2003 |
| EP | 0 734 738 B1 | 10/2003 |
| EP | 1 049 503 B1 | 10/2003 |
| FR | 2 830 764 A1 | 4/2003 |
| FR | 2 830 765 A1 | 4/2003 |
| FR | 2 832 932 A | 6/2003 |
| GB | 2 282 069 A | 3/1995 |
| JP | 2001193714 | 12/2002 |
| WO | WO 01/41841 A2 | 6/2001 |
| WO | WO 01/41841 A3 | 6/2001 |
| WO | WO 01/60435 A1 | 8/2001 |
| WO | WO 01/85238 A2 | 11/2001 |
| WO | WO 02/072171 A2 | 9/2002 |
| WO | WO 02/089878 A1 | 11/2002 |
| WO | WO 02/098480 A2 | 12/2002 |
| WO | WO 02/098494 A2 | 12/2002 |
| WO | WO 02/098494 A3 | 12/2002 |
| WO | WO 03/000322 A1 | 1/2003 |
| WO | WO 03/000323 A1 | 1/2003 |
| WO | WO 03/011378 A1 | 2/2003 |
| WO | WO 03/015852 A1 | 2/2003 |
| WO | WO 03/022335 A2 | 3/2003 |
| WO | WO 03/033059 A1 | 4/2003 |
| WO | WO 03/033060 A1 | 4/2003 |
| WO | WO 03/041766 A2 | 5/2003 |
| WO | WO 03/045476 A1 | 6/2003 |
| WO | WO 03/045480 A1 | 6/2003 |
| WO | WO 03/045481 A1 | 6/2003 |
| WO | WO 03/063934 A1 | 8/2003 |
| WO | WO 03/068297 A1 | 8/2003 |
| WO | WO 03/068298 A1 | 8/2003 |

* cited by examiner

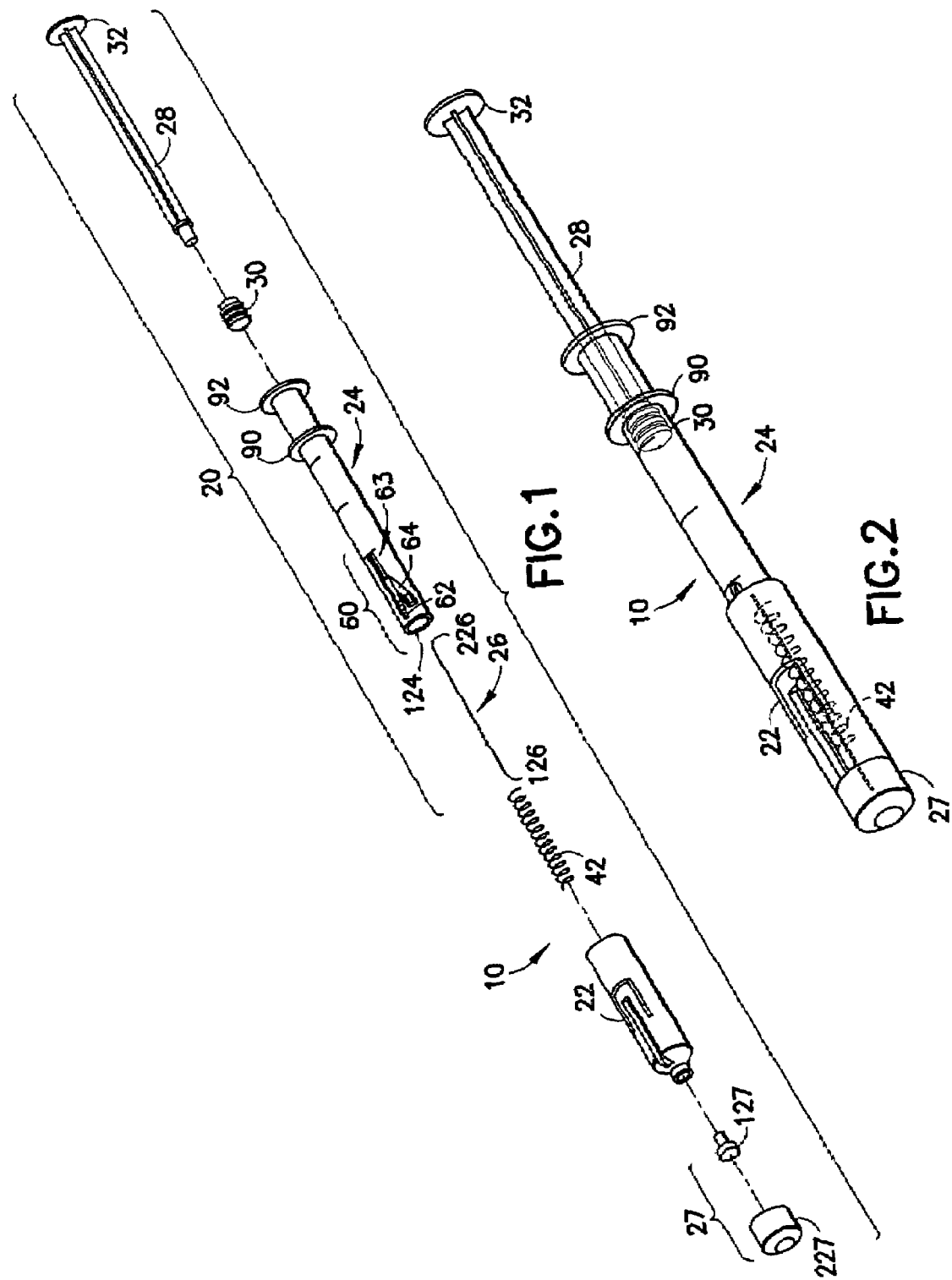

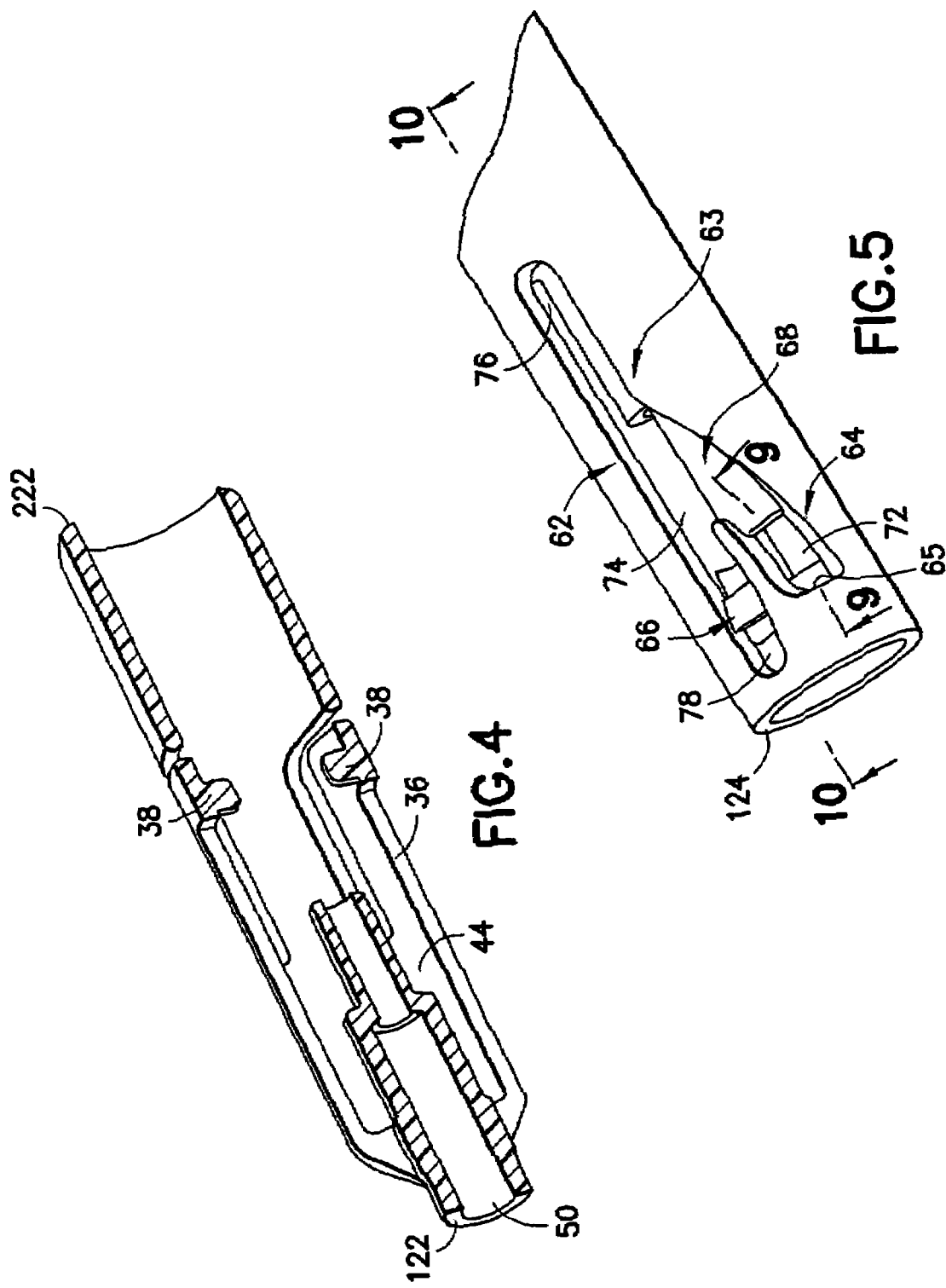

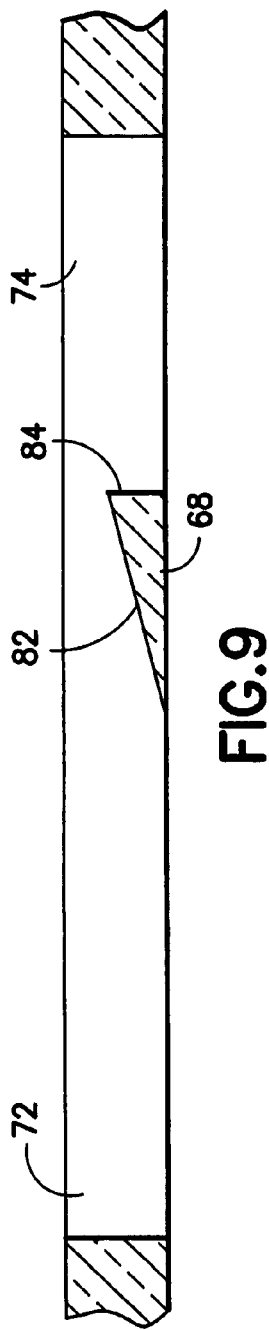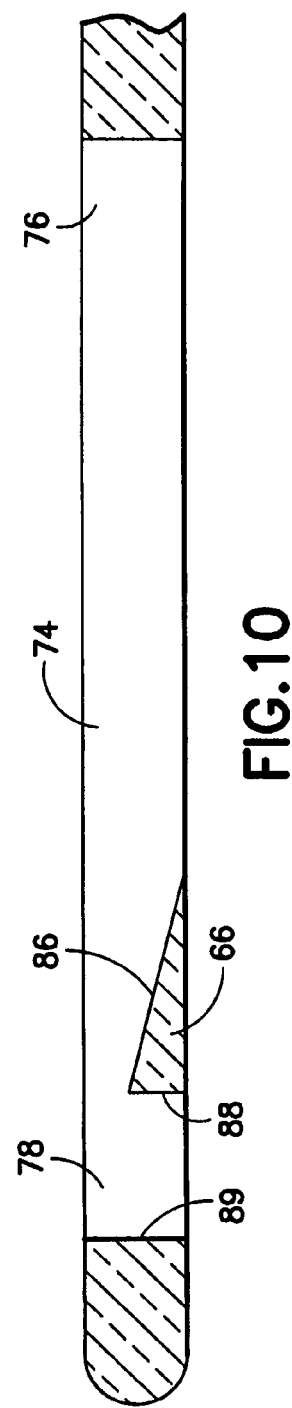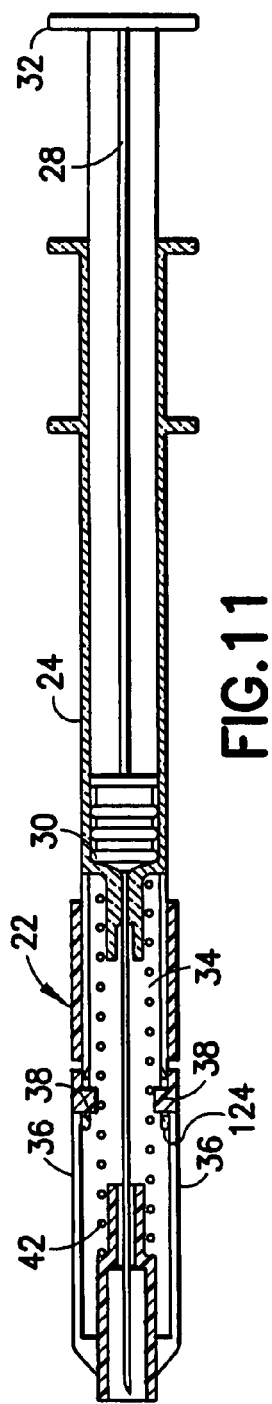

SAFETY SHIELD SYSTEM FOR A SYRINGE

BACKGROUND OF THE INVENTION

1. Field of the Invention

The present invention relates to a prefilled medical device for delivering a dose of medicament by injection and having an integral shield system for preventing accidental needle sticks after use. More particularly, the present invention is directed to a syringe assembly including a safety shield system.

2. Description of the Related Art

Syringes used for the delivery of medicaments to patients are well known. Oftentimes syringes are prefilled with a dosage of a medicament or other substance by a pharmaceutical manufacturer and then distributed to end users such as health care professionals or patients for administration of the prefilled medicament. Such syringes typically include a cylindrical hollow barrel which may be formed of a glass or plastic material and which includes the medicament. One end of the barrel is fitted with a fixed or removable hollow needle, and the other end of the barrel receives a plunger having a stopper which is slidable with respect to the barrel for delivery of the medicament to the hollow needle, i.e., to urge the medicament toward and out of the needle. A syringe assembly, which typically includes the above-described components, is usually stored with a removable needle cover which protects the needle from damage during storage and handling. Prior to use, the needle cover is removed to expose the needle.

To prevent a syringe user and, in particular, a health care professional from inadvertent sticks by the needle after use of the syringe on a patient, the syringe assembly may incorporate a safety shield which forms a guard to cover the needle after use. Some such shields are spring activated for imparting a telescoping-like deployment action to the safety shield. Certain attributes to be considered in such syringe assemblies are that the shield should be intuitive and easy to use, should preferably provide consistent and reliable shield deployment, and should be operable with one hand. Other attributes are that such syringe assemblies require no change in current medicament delivery techniques, allow for dose adjustment, are preferably autoclavable, and allow for the inspection of contents before and after activation of the shield. Moreover, the use of the shield must not detrimentally affect processing and filling of the syringe at the pharmaceutical company, the assembly (i.e., syringe assembly and safety shield) must be easy to manufacture, must prevent accidental activation, and must limit the possibility of incurring cosmetic or structural damages.

SUMMARY OF THE INVENTION

The present invention relates to a medical device including a syringe assembly and incorporating a safety shield for covering the needle of the syringe assembly after administration of a dosage of medicament. The safety shield is automatically activated upon insertion of the needle of the syringe to a medicament delivery depth in a patient.

According to the present invention, the medical device for delivering a medicament to a patient includes a syringe having a barrel with a forward end and a rear end and defining a reservoir within which the medicament may be contained. A needle or needle cannula (those terms being used interchangeably herein) having a forward tip is provided proximate the forward end of the barrel and is in fluid communication with the reservoir. A shield is releasably mounted on a front portion of the barrel at a first position. An urging member is arranged between the barrel and the shield for urging the shield forward relative to the syringe assembly. The urging member may be, by way of non-limiting example, a coil spring. The shield is movable from the first position to a second position under the influence of the urging member when the needle cannula is inserted into a patient for delivery of the medicament by interaction with the patient's skin. After delivery of the medicament, the shield is moveable from the second position to a third position, by the urgency of the urging member, upon removal of the needle cannula from the patient. When the shield is in the third position, the forward tip of the needle cannula is covered by the shield by a sufficient amount to prevent the tip of a finger from contacting the needle tip.

The syringe includes a plunger having a first end with a stopper positioned in the reservoir. A second end of the plunger has a thumb pad or thumb press area for receiving medicament delivery pressure for pressing the plunger into the syringe barrel to deliver the medicament. The terms "thumb pad" and "thumb press area" are used interchangeably herein and designate a region coupled to or otherwise formed on an end of the plunger and which may be depressed by the thumb or finger of a user during use of the medical device.

The medical device may include a device for preventing the shield from moving back to the first position from the second position.

The shield defines a track arrangement having an entry track and a lock-out track. The barrel includes a pin mounted on a lever arm which is guidably received in the track arrangement. The entry track and the lock-out track are joined at an intersection. The pin is guided in the entry track when the shield moves from the first position to the second position and the pin is guided in the lock-out track when the shield moves from the second position to the third position.

A blocking element may be arranged in the entry track proximate the intersection for blocking reentry of the pin into the entry track once the pin has been aligned with the lock-out track. The blocking element may have an inclined surface facing the entry track for facilitating movement of the pin from the entry track to the lock-out track while preventing return movement, i.e. movement of the pin from the lock-out track back to the entry track.

The medical device may also include a locking device for locking the shield in the third position. The locking device may comprise an element that is similar to the blocking element having an inclined surface for facilitating movement of the pin in one direction, i.e. along the lock-out track to a fully-deployed position of the shield, and blocking movement of the pin in the reverse direction.

The lock-out track may extend parallel to the longitudinal axis of the medical device and the entry track may extend at least partially in the circumferential direction such that the shield rotates with respect to the longitudinal axis as the shield moves from the first position to the second position. Alternatively, the entry track may extend parallel to the longitudinal axis of the medical device and the lock-out track may extend at least partially in the circumferential direction such that the shield rotates with respect to the longitudinal axis as the shield moves from the second position to the third position. As a further alternative, both the entry track and the lock-out track may extend at least partially in the circumferential direction, such that the shield rotates as it moves from the first position to the second position and from the second position to the third position.

The barrel may comprise a cylindrical portion extending forward of the reservoir on which the track arrangement is defined. The cylindrical portion may be formed unitarily with the barrel.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the drawings, wherein like reference characters denote similar elements throughout the several views:

FIG. 1 is an exploded perspective view of the components of a medical device according to an embodiment of the present invention;

FIG. 2 is a perspective view of the assembled medical device of FIG. 1;

FIG. 4 is a perspective sectional view of a shield of the medical device of FIG. 1 along a longitudinal axis of the shield;

FIG. 5 is a perspective view of a forward end of a syringe barrel of the medical device of FIG. 1;

FIG. 9 is a sectional view of the entry track in the syringe barrel of the medical device of FIG. 1;

FIG. 10 is a sectional view of the lock-out track in the syringe barrel of the medical device of FIG. 1;

FIG. 11 is a longitudinal sectional view of the medical device of FIG. 1 after use;

DETAILED DESCRIPTION OF THE PRESENTLY PREFERRED EMBODIMENTS

Figure 3:
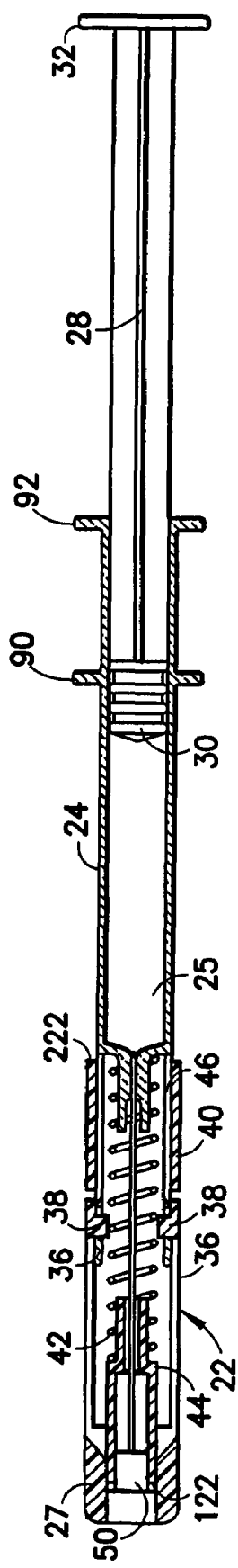
FIG. 3 is a longitudinal cross-sectional view of the medical device of FIG. 1 in a state prior to use.

FIGS. 1-3 show a medical device 10 for delivery of a medicament into a patient constructed in accordance with an embodiment of the present invention. As used herein, the term "medicament" is intended to refer to any drug substance, vaccine, or other liquid substance that is injected into the patient. The medical device 10 includes a syringe 20 which can be prefilled with the mendicant to be delivered, and a shield 22 which surrounds a front end of the syringe 20.

The syringe 20 includes a cylindrical barrel 24 defining a reservoir 25 (see FIG. 3) within which the medicament may be held prior to use of the medical device 10. The syringe 20 also includes a needle cannula 26 having a forward tip 126 and a rearward end 226 in fluid communication with the reservoir 25. The needle cannula 26 may be permanently connected to a front end of the barrel 24 using an adhesive, glue, interference fit or other known or hereafter developed material or technique, or it may be detachable from the barrel such as for example, using a luer-type connection. A front section 60 of the barrel 24 defines tracks 62, 64 in an outer surface thereof which interact with the shield 22 as explained in detail below. The barrel 24 is preferably made of plastic. However, the barrel 24 may also be made of glass. In an alternative embodiment, the barrel 24 may be made of glass with the front section 60 made of plastic. A plunger rod 28 has a first end inserted in the barrel 24 with a stopper or piston 30 arranged on the first end that is movable with the plunger 28 within the barrel 24. A second end of the plunger rod 28 includes a thumb pad 32 used for receiving pressure from the user's thumb for moving the piston 30 into and within the barrel 24. Finger rests 90, 92 on the barrel in the form of flanges provide ergonomic grips for holding the medical device 10 during insertion of the needle cannula 26 and during the application of medicament delivery force to the thumb pad 32. Although these finger rests 90, 92 are depicted as flanges, any other designs may be used such as, for example, radial projections.

As further shown in FIGS. 1 and 2, a removable needle shield 27 is disposed over the needle cannula 26 on the front end of the shield 22 to protect the needle from damage during the handling of the medical device 10, and to protect users from being stuck by the needle prior to its intended use. The removable needle shield 27 is arranged on the front end of the shield 22. The needle shield 27 preferably includes a pliable part 127 and a rigid part 227.

As described below, the shield 22 is movable from an initial or first position, in which the forward tip 126 of the needle cannula 26 extends beyond a front end 122 of the shield 22, to an intermediate or second position, and then from the intermediate position to a shielded or third position in which the forward tip 126 of the needle cannula 26 is contained within the shield body 22. An urging member 42, such as, for example, a coil spring or biasing arm, urges the shield forward relative to the barrel 24.

The various component parts of the inventive medical device 10 will now be discussed in further detail. The shield 22 is depicted in FIG. 4 and is essentially cylindrically-shaped. The front end 122 of the shield defines a channel passage or guide hole 50 through which the needle cannula 26 extends in the initial position. The shield 22 also includes an upper and lower lever arm 36 running longitudinally along the outer surface of the shield 22 (only the free end of the upper lever arm 36 is visible in FIG. 4). The free end of each of the lever arms 36 includes a pin 38 extending radially inward. Although two lever arms 36 are shown in the preferred embodiment, the shield 22 may include one or more lever arms 36. A spring seat 44 is arranged proximate the front end 122 for receiving an end of the urging member 42 as described below.

Figure 6:
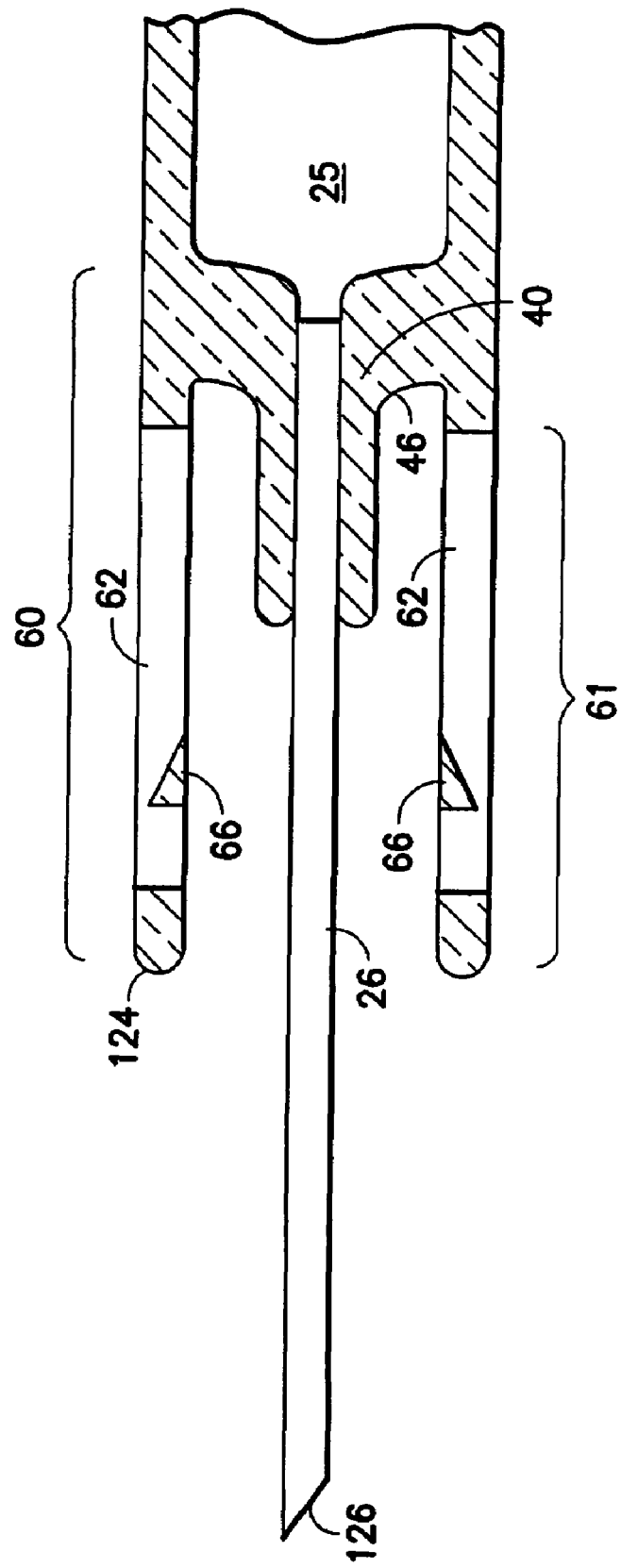
FIG. 6 is a partial longitudinal sectional view of the forward end of the syringe barrel of FIG. 5.

The front end portion 60 of the barrel 24 is shown in FIGS. 5 and 6. The front end portion 60 includes a needle holder 40 in which the needle cannula 26 is mounted, and a cylindrical portion 61 is arranged in front of the reservoir 25. The cylindrical portion 61 may be added to the front of a conventional syringe barrel using an adhesive or other more permanent connection. The connection may also be, by way of non-limiting example, made by one of press fitting, spin welding, heat stake, or threading. The front end portion 60 defines two intersecting pair of tracks 63 on the cylindrical portion 61 corresponding to the two lever arms 36 (only one pair of tracks 63 is visible in FIG. 6). Each pair of tracks 63 comprises an entry track 64 and a lock-out track 62 which intersect with each other. The pin 38 of each lever 36 is received in one of the lock-out and entry tracks 62, 64 of a corresponding one of the pair of tracks 63. In the initial position of the medical device shown in FIGS. 1-3 in which the front tip 126 of the needle cannula 26 extends past the front end 122 of the shield 22, the pins 38 are located in end areas 72 (see FIG. 5) of the entry track 64 proximate the front end 124 of the barrel 24. The urging member 42 is arranged between a front facing surface 46 (see FIG. 6) of the needle holder 40 and the spring seat 44 (see FIG. 4) arranged at the front end 122 of the shield 22 for urging the pins 38 against the front surfaces 65 of the entry tracks 64 proximate the end areas 72. Accordingly, the interaction of the pins 38 and the front surfaces 65 of the entry tracks 64 prevents the shield 22 from sliding off of the front of the barrel 24 under the urgency of the urging member 42.

Figure 7:
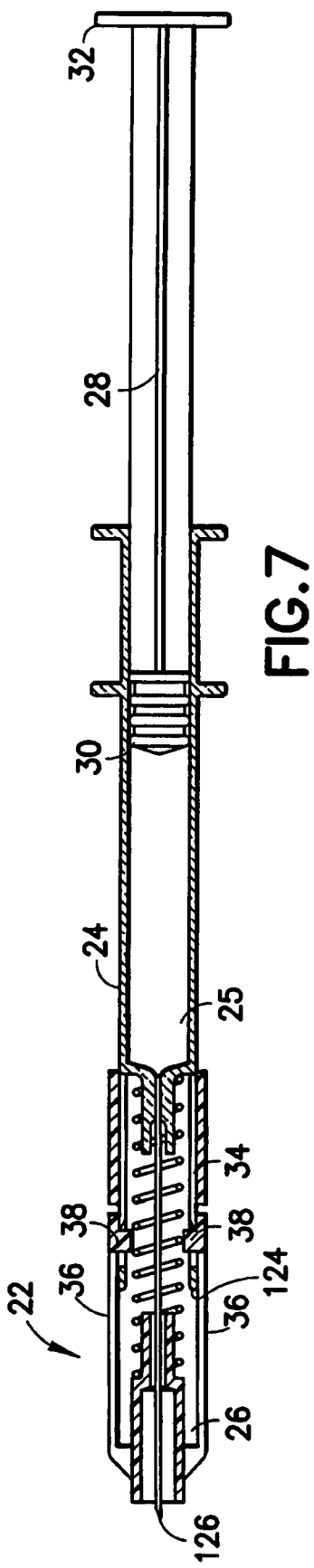
FIG. 7 is a longitudinal sectional view of the medical device of FIG. 1 in a ready to use state.

Prior to use of the medical device 10, the removable needle shield 27 is separated from the medical device 10. At this stage, the shield 22 remains in the position shown in FIG. 3 wherein which the pins 38 are in the end areas 72 of the entry tracks 64, i.e. the shield is in the first position. In FIG. 7, a portion of the needle cannula 26 proximate the forward tip 126 is exposed in the first position. However, the forward tip 126 is not required to be exposed in this position. Therefore, the forward tip 126 may alternatively be covered by or contained in the shield 22 in the first position.

Figure 8:
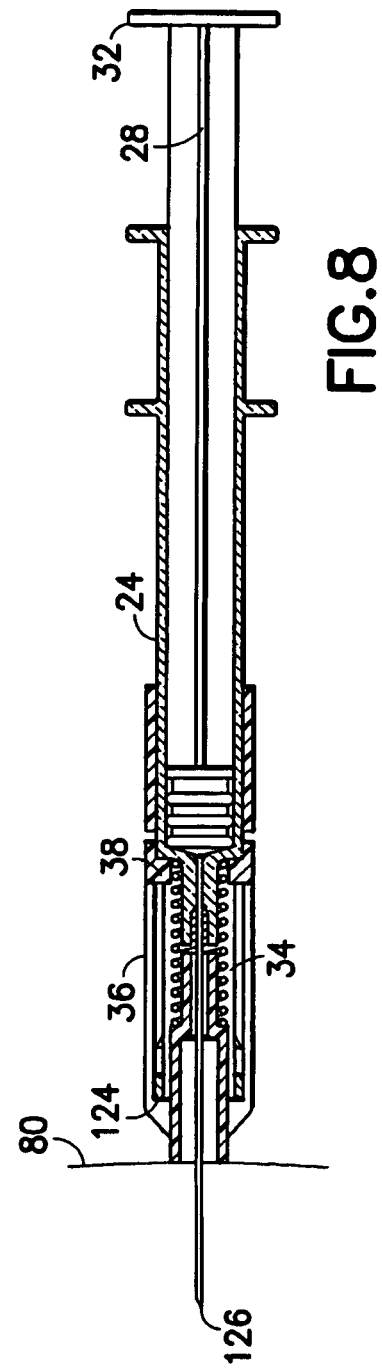
FIG. 8 is a longitudinal sectional view of the medical device of FIG. 1 during use.

As the needle cannula 26 is inserted into a patient to deliver the medicament, the front end 122 of the shield 22 contacts the skin 80 of the patient. As the needle cannula 26 continues to be inserted into the patient, the shield 22 is pushed, by a force applied by the patient's skin, rearward on the syringe barrel 24 toward the thumb pad 32 until the needle cannula 26 is fully inserted in the patient as shown in FIG. 8. During the movement of the shield 22, each of the pins 38 moves along a respective entry track 64. During this movement, each pin 38 moves from end area 72 over a one-way entry step 68 and into a central position 74. This path is shown in FIG. 9 which is a sectional view along the longitudinal axis of the entry track 64. As each pin 38 passes over the one-way entry step 68, it moves along an inclined portion 82 and the lever arm 36 resiliently flexes radially outward in a direction traverse to the axis of the medical device 10. Once the pin 38 passes over the one-way entry step 68, the lever arms 36 return to their original positions and the pin 38 is, at that point, located in the central position 74 of the lock-out track 62 with the shield 22 being in a second position. When the pins 38 pass the one-way entry steps 68 and enter the central positions 74 of the lock-out tracks 62, the shield 22 is actuated and a blocking surface 84 of the one-way entry step 68 blocks reentry of the pins 38 into the entry tracks 64. Even though the shield 22 is actuated in this position, the needle cannula 26 may be inserted further into the patient so that the shield 22 is pushed further back against the force of the urging member 42 and onto the barrel 24. As this occurs, the pins 38 move toward the rear ends 76 of the lock-out paths 62.

After the medicament is delivered, the needle cannula 26 is removed from the patient. This provides clearance for the shield 22, whereupon the shield is then urged, by the force of the fully-charged urging member 42, to a third position in which the shield body 22 extends beyond the forward tip 126 of the needle cannula 26. As shown in FIGS. 5 and 10, each lock-out path 62 also includes a one-way lock-out step 66 which has an inclined surface 86 and a blocking surface 88. The inclined surface 86 allows the pin 38 guided in the lock-out track 62 to move toward the forward end 78 of the lock-out track 62 as the shield 22 moves to the shielded position. When the shield 22 reaches the shielded position, the pin 38 is in the forward area 78 between the one-way lock-out step 66 and a forward end 89 of the lock-out track 62. The blocking surface 88 prevents the pin 38 from moving out of the forward end 78, thereby locking the shield 22 in the second position.

Figure 12:
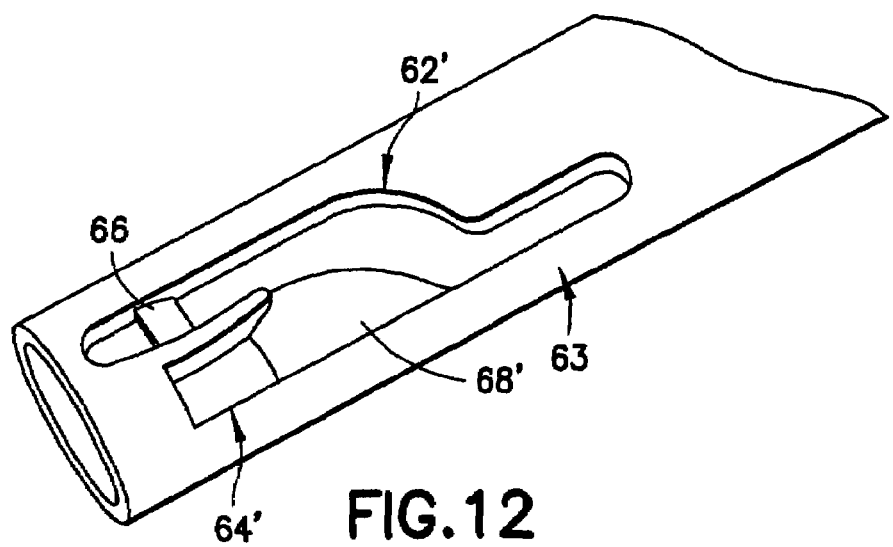
FIG. 12 is a perspective view of an alternative embodiment of the shield of the medical device according to the present invention.

In the embodiment of FIGS. 1-11, the entry track 64 is curved such that as the pin 38 is moved along the entry track 64 during insertion of the needle cannula 26 in the patient, the shield 22 is rotated about the longitudinal axis of the device 10 until the pin 38 enters the central area 74 of the lock-out track 62. The lock-out track 62 extends parallel to the longitudinal axis so that the shield does not rotate during movement of the pin in the lock-out track 62. In an alternative embodiment shown in FIG. 12, the entry track 64' is arranged parallel to the longitudinal axis of the shield so that the shield 22 does not rotate during insertion of the needle cannula 26 into the patient. Rather, the shield 22 rotates as the pin 38 moves along the lock-out track 62' during the withdrawal of the needle cannula 26 from the patient. In each of the embodiments of FIGS. 1-12, one of the entry track 64, 64' and the lock-out track 62, 62', extends parallel to the longitudinal axis of the device 10. However, there is no requirement that one of the tracks be parallel to the longitudinal axis of the device 10. Accordingly, both the entry and lock-out tracks may extend at an angle relative to the longitudinal axis of the device 10 such that the shield 22 rotates during movement from the first to the second position and from the second position to the third position.

Figure 13:
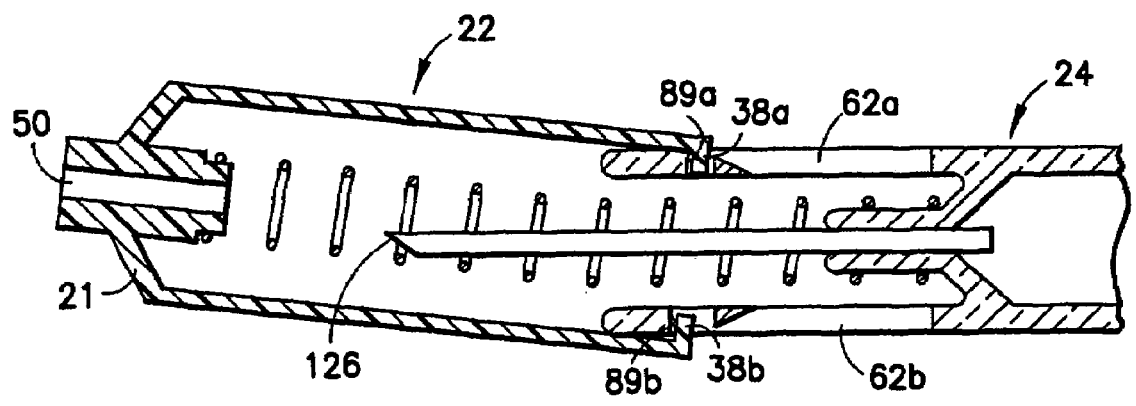
FIG. 13 is a partial longitudinal sectional view of a further embodiment of the shield and barrel according to the present invention.

FIG. 13 shows another alternative embodiment in which the end surfaces 89a, 89b of lock-out tracks 62a, 62b are axially offset from each other. When the shield 22 is pushed into the shielded position, the pin 38a first contacts the end surface 89a which causes the shield 22 to pivot about the initial point of contact at end surface 89a until the pin 38b rests on the end surface 89b (or until the shield 22 contacts the needle cannula), as shown in FIG. 13. In this position, the shield 22 is askew relative to the needle cannula 26 and the needle cannula 26 is not aligned with the hole 50 in the shield through which it was formerly inserted. This configuration prevents inadvertent sticks because when the shield 22 is pressed into the barrel, the forward tip 126 of the needle cannula 26 is not aligned with the hole 50 but, instead, contacts a front wall 21 of the shield 22 to maintain the needle tip 126 within the shield 22. This embodiment may be used with or without the lock-out step 66 described above.

Figure 14:
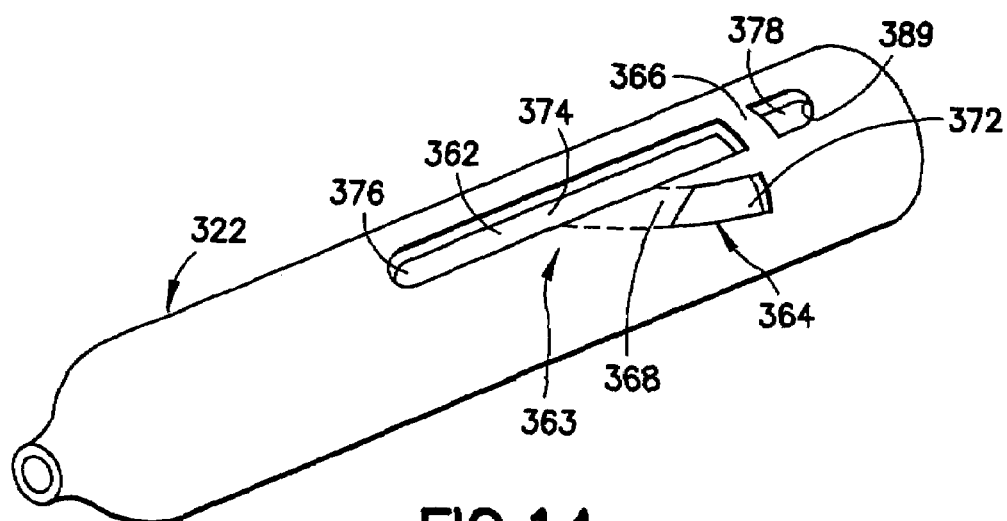
FIG. 14 is a perspective view of a shield according to yet another embodiment of the present invention.
Figure 15:
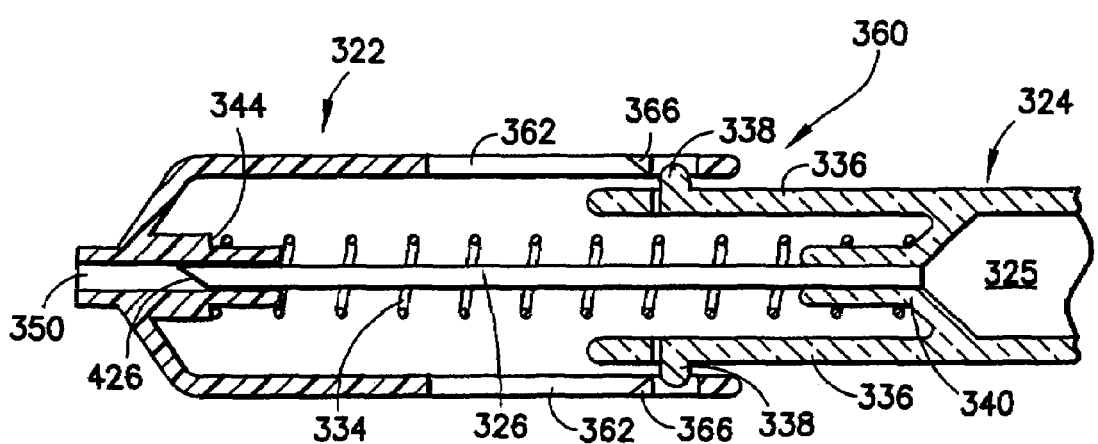
FIG. 15 is a partial longitudinal sectional view of the shield of FIG. 14 with the barrel of the syringe assembly.

FIGS. 14-15 show a further embodiment in which pairs of tracks 363 are defined on a shield 322, each pair of tracks 363 including an entry track 364 and a lock-out track 362. A front portion 360 of a syringe barrel 324 includes lever arms 336 with radially outwardly extending pins 338 or projections which are received in the tracks 363. Similarly to the above embodiment disclosed in FIGS. 1-11, the shield 322 is arranged in a first position in which a forward tip 426 of a needle cannula 326 is exposed as shown in FIG. 7. In the first position of the shield 322, the pins 338 are in end areas 372 of the entry tracks 364. As the needle cannula 326 is inserted into a patient for delivery of the medicament, the skin of the patient pushes the shield 322 against the urgency of the urging member 334 such that the pin 338 is guided along the entry track 364 and over the inner surface of the step 368. The entry track 364 is similar to the entry track 64 shown in FIG. 9 and extends across the inner surface of the step 368 to the lock-out track 362 as indicated by the dotted lines in FIG. 14. Once the pins 338 enter the lock-out tracks 362, the steps 368 block reentry of the pins 338 into the entry tracks 364. The shield 322 may be pushed further onto the barrel 324 (by continued forward movement of the needle cannula 326 into the patient) until the pins reach the end areas 376. When the needle cannula 326 is removed from the patient, the urging member 334 urges the shield 322 forward until the pins 338 rest against end surfaces 389 of the lock-out tracks 362. As described above regarding lock-out step 66 in FIGS. 5 and 6, each lock-out track 362 includes a lock-out step 366 which allows pin 338 to move toward the end area 378 and blocks the pin 338 from moving out of the end area 378 once it has entered the end area 378.

A description of an exemplary usage of the medical device 10 of the present invention will now be provided with respect to FIGS. 1-11. It should be understood by a person of ordinary skill in the art that the following description is provided as an illustrative and non-limiting example. The health care professional receives the inventive medical device 10 prefilled with a desired dosage of medicament. Immediately prior to use, the needle shield 27 is removed and the forward tip 126 of the needle cannula 26 is exposed. The health care professional pierces the patient's skin with the forward tip 126 of the needle cannula 26 and inserts the needle cannula 26 to the proper penetration depth. When the needle cannula 26 is first inserted, the front end 122 of the shield 22 contacts the patient's skin and the shield is in the first position. As the needle cannula 26 is further inserted into the patient, the shield 22 moves rearward in the direction of the barrel 24 from the initial position of the shield to an intermediate or the second position. This causes charging of the urging member 42. During this movement, the pin 38 of the shield 22 is guided in the entry track 64, over the step 68 and into the lock-out track 62 at which point the shield 22 is in the intermediate or the second position. As the needle cannula is further inserted, the shield is pushed further onto the barrel and the pin 38 is guided in the lock-out track 62 toward end area 76. This results in complete charging of the urging member 42.

Once the needle cannula 26 is fully inserted into the patient, the health care professional depresses the thumb pad 32 to cause the plunger rod 28 and piston 30 to move within the reservoir 25. As the plunger rod 28 and piston 30 are moved into the reservoir, the medicament is caused to be expelled from the reservoir 25, through the needle cannula 26, and into the patient. After delivery of the medicament, the health care worker withdraws the needle cannula 26 from the patient. As the needle cannula is withdrawn, the urging member urges the shield 22 forward until the shield reaches the third position in which the shield covers the forward tip 126 of the needle cannula 26, thus preventing undesired and inadvertent exposure of the health care professional to the contaminated forward tip 126. The used medical device may then be disposed of in a suitable sharps disposal container.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements which perform substantially the same function in substantially the same way to achieve the same results are within the scope of the invention. Moreover, it should be recognized that structures and/or elements shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A medical device for delivering a medicament to a patient, comprising:
    a syringe assembly comprising:
        a barrel having a forward end and a rear end and defining a reservoir within which the medicament may be contained;
        a needle cannula having a forward tip and being coupled to said forward end of said barrel and in fluid communication with said reservoir; and
        a plunger having a first end with a stopper positioned in said reservoir and a second end having a thumb pad for receiving medicament delivery pressure for causing said plunger to move within said reservoir to expel the medicament from said reservoir;
    a shield releasably mounted on a front portion of said barrel at a first position; and
    an urging member for urging said shield in a forward direction relative to said syringe assembly, wherein one of said shield and said barrel defines two track arrangements on opposing sides of said one of said shield and said barrel, each of said track arrangements having an entry track having an end joined to a lockout track at an intersection, a first portion of said lockout track extending beyond said intersection to a first end of said lockout track and a second portion of said lockout track extending beyond said intersection to a second end of said lockout track, and the other of said shield and said barrel includes pins arranged on resilient lever arms and guidable in respective ones of said track arrangements,
    said shield being movable by interaction with an area proximate a needle cannula insertion point on a patient's skin from said first position to a second position against the urgency of said urging member when said needle cannula is inserted into a patient for delivery of the medicament, wherein, in each of said track arrangements, said pin moving from a first pin position along said entry track at least to the intersection and into a second pin position in said lock-out track during movement of said shield from the first position to the second position, and
    said shield being moveable from said second position to a third position by the urgency of said urging member upon removal of said needle cannula from said patient, wherein, in each of said track arrangements, said pin moving along said lockout track from said second pin position to a third pin position solely by the urgency of said urging member during movement of said shield from said second position to said third position, the forward ends of said lockout tracks being axially offset so that said shield is held askew relative to said needle cannula by the urgency of said urging member when said shield is in the third position, and
    wherein said forward tip of said needle cannula is covered by said shield when said shield is in said third position, wherein said one of said shield and said barrel further comprises a blocking element arranged at said end of said entry track proximate said intersection in at least one of said track arrangement, said blocking element having a fixed blocking surface facing said lock-out track of said at least one of said track arrangements and blocking reentry of the associated one of said pins into said entry track from said lock-out track.

2. The medical device of claim 1, further comprising means for preventing said shield from moving back to said first position after said shield is moved to said second position.

3. The medical device of claim 1, wherein said pins are arranged proximate said free ends of said lever arms.

4. The medical device of claim 1, wherein said blocking element of said at least one of said track arrangements further comprises an inclined surface facing said entry track, the one of said pins in said at least one of said track arrangements sliding over said inclined surface and bending said associated resilient lever as said pin in said at least one of said track arrangements slides over said inclined surface, thereby allowing movement of said shield from said entry track toward said lock-out track.

5. The medical device of claim 1, wherein said one of said shield and barrel comprises a locking device for locking the shield in said third position.

6. The medical device of claim 5, wherein said lock-out tracks are defined between first and second end surfaces at the first and second ends thereof, said pins being guided toward said first ends when said shield is moved toward said third position, said locking device comprising a one-way step arranged proximate said first end of one of said lock-out tracks such that the one of said pins in said one of said lock-out tracks is arranged between said one-way step and said first end surface of said one of said lock-out tracks when said shield is in said third position.

7. The medical device of claim 6, wherein said one-way step comprises a blocking surface facing said first end of said one of said lock-out tracks, said blocking surface preventing said one of said pins in said one of said lock-out tracks from moving from said first end toward said second end and thereby locking said shield in said third position.

8. The medical device of claim 7, wherein said one-way step comprises an inclined surface facing said second end of said one of said lock-out tracks, said one of said pins in said one of said lock-out tracks sliding over said inclined surface as said shield moves toward said second position, thereafter allowing movement of said one of said pins in said one of said lock-out tracks toward said first end of said lock-out track.

9. The medical device of claim 1, wherein one of said entry track and said lock-out track of each of said track arrangements extends parallel to a longitudinal axis of said medical device.

10. The medical device of claim 9, wherein, in each of said track arrangements, said lock-out track extends parallel to the longitudinal axis of said medical device and said entry track extends at least partially in the circumferential direction such that the shield rotates as the shield moves from said first position to said second position.

11. The medical device of claim 9, wherein, in each of said track arrangements, said entry track extends parallel to the longitudinal axis of said medical device and said lock-out track extends at least partially in the circumferential direction such that the shield rotates about the longitudinal axis as the shield moves from said second position to said third position.

12. The medical device of claim 1, wherein said urging member is a spring.

13. The medical device of claim 1, wherein said barrel is plastic.

14. The medical device of claim 1, wherein said barrel is glass.

15. The medical device of claim 1, wherein said barrel comprises a cylindrical portion extending forward of said reservoir, said cylindrical portion defining said track arrangements.

16. The medical device of claim 15, wherein said cylindrical portion is formed unitarily with said barrel.

17. The medical device of claim 15, wherein said cylindrical portion is plastic and a remainder of said barrel is glass.

18. The medical device of claim 1, wherein, each of said pins comprises a radial projection.

19. The medical device of claim 2, wherein, in each of said track arrangements, said third pin position is at the first end of said lock-out track, and said pin is movable from said second pin position to the second end of said lock-out track after said pin enters said lock-out track at said second position, whereby said means for preventing prevents said pin from entering said entry track before said shield reaches a rearmost position of said shield relative to said syringe assembly.

20. A combination comprising a medical syringe and a safety shield assembly, said medical syringe comprising a barrel having a forward end and a rear end and defining a reservoir within which the medicament may be contained, a needle cannula having a forward tip and being coupled to said forward end of said barrel and in fluid communication with said reservoir, and a plunger having a first end with a stopper positioned in said reservoir and a second end having a thumb pad for receiving medicament delivery pressure for causing said plunger to move within said reservoir to cause the medicament to be expelled from said reservoir; and said safety shield assembly comprising a shield releasably mounted on a front portion of said barrel at a first position, and an urging member for urging said shield in a forward direction relative to said barrel, wherein one of said shield and said barrel defines two track arrangements on opposing sides of said one said shield and barrel, each of track arrangements having an entry track with an end joined to a lockout track at an intersection, a first portion of said lockout track extending beyond said intersection to a first end of said lockout track and a second portion of said lockout track extending beyond said intersection to a second end of said lockout track, and the other of said shield and said barrel includes a radial projections arranged on resilient lever arms and guidably inserted in respective ones of said track arrangements, said shield being movable by interaction with an area on a patient's skin proximate a needle cannula insertion point from said first position to a second position against the urgency of said urging member when said needle cannula is inserted into a patient for delivery of the medicament, wherein, in each of said track arrangements, said radial projection moving from a first projection position along said entry track at least to the intersection and into a second projection position in said lock-out track during movement of said shield from the first position to the second position, and said shield being moveable from said second position to a third position by the urgency of said urging member upon removal of said needle cannula from said patient, wherein said forward tip of said needle cannula is covered by said shield when said shield is in said third position, wherein, in each of said track arrangements, said radial projection moving in said lock-out track from said second projection position to a third projection position solely by the urgency of said urging member during movement of said shield from the second position to the third position, the forward ends of said lockout tracks being axially offset so that said shield is held askew relative to said needle cannula by the urgency of said urging member when said shield is in the third position, and wherein said one of said shield and said barrel further comprises a blocking element arranged at said end of said entry track proximate said intersection in at least one of said track arrangements, said blocking element having a fixed blocking surface facing said lock-out track of said at least one of said track arrangements, and blocking reentry of the associated one of said pins into said entry track from said lock-out track.

21. The combination of claim 20, wherein said barrel is plastic.

22. The combination of claim 20, wherein said barrel is glass.

23. The combination of claim 20, wherein said barrel comprises a cylindrical portion extending forward of said reservoir, said cylindrical portion defining said track arrangements.

24. The combination of claim 23, wherein said cylindrical portion is formed unitarily with said barrel.

25. The combination of claim 23, wherein said cylindrical portion is plastic and the remainder of said barrel is glass.

26. The combination of claim 20, further comprising a blocking element in said entry track of at least one of said track arrangements preventing said shield from moving back to said first position after said shield is moved to said second position, wherein, in each of said track arrangements, said third pin position is at one of the ends of said lock-out track, and said pin is movable from said second pin position to the other one of the ends of said lock-out track after said pin enters said lock-out track at said second position, whereby said blocking element prevents said pin from entering said entry track before said shield reaches a rearmost position of said shield relative to said barrel.

27. A shield assembly for connection to a syringe barrel for preventing inadvertent needle sticks after use of the syringe, the shield system comprising a cylindrical portion connectable to a front end of the syringe barrel, a shield releasably mounted on said cylindrical portion at a first position, and an urging member for urging said shield in a forward direction relative to the syringe barrel, wherein one of said shield and said cylindrical portion defines two track arrangements on opposing sides of said one of said shield and said barrel, each of said track arrangements, having an entry track with an end joined to a lockout track at an intersection, a first portion of said lockout track extending beyond said intersection to a first end of said lockout track and a second portion of said lockout track extending beyond said intersection to a second end of said lockout track, and the other of said shield and said cylindrical portion includes pins arranged on resilient lever arms and guidably inserted in said track arrangements, said shield being movable by interaction with an area proximate a needle cannula insertion point on a patient's skin from said first position to a second position against the urgency of said urging member when a needle cannula of the syringe is inserted into a patient for delivery of the medicament, wherein, in each of said track arrangements, said pin moving from a first pin position along said entry track at least to the intersection and into a second pin position in said lock-out track during movement of said shield from the first position to the second position, and said shield being moveable from said second position to a third position by the urgency of said urging member upon removal of the needle cannula from the patient to cover the tip of the needle cannula connected to the forward end of the syringe barrel, wherein, in each of said track arrangements, said pin moving along said lockout track from said second pin position to a third pin position solely by the urgency of said urging member during movement of said shield from said second position to said third position, the forward ends of said lockout tracks being axially offset so that said shield is held askew relative to said needle cannula by the urgency of said urging member when said shield is in the third position, and wherein said one of said shield and said barrel further comprises a blocking element arranged at said end of said entry track proximate said intersection in at least one of said track arrangements, said blocking element having a fixed blocking surface facing said lock-out track of said at least one of said track arrangements and blocking reentry of the associated one of said pins into said entry track from said lock-out track.

28. The shield assembly of claim 27, further comprising means for preventing said shield from moving back to said first position after said shield is moved to said second position.

29. The shield assembly of claim 27, wherein said pins is arranged proximate said free ends of said lever arms.

30. The shield assembly of claim 27, wherein one of said entry track and said lock-out track of each of said track arrangements, extends parallel to a longitudinal axis of said medical device.

31. The medical device of claim 30, wherein, in each of said track arrangements, said lock-out track extends parallel to said longitudinal axis of said medical device and said entry track extends at least partially in the circumferential direction such that the shield rotates as the shield moves from said first position to said second position.

32. The medical device of claim 30, wherein, in each of said track arrangements, said entry track extends parallel to said longitudinal axis of said medical device and said lock-out track extends at least partially in the circumferential direction such that the shield rotates as the shield moves from said second position to said third position.

33. The shield assembly of claim 27, further comprising a blocking element in at least one of said track arrangements preventing said shield from moving back to said first position after said shield is moved to said second position, wherein, in each of said track arrangements, said third pin position is at one of the ends of said lock-out track, and said pin is movable from said second pin position to the other one of the ends of said lock-out track after said pin enters said lock-out track at said second position, whereby said blocking element prevents said pin from entering said entry track before said shield reaches a rearmost position of said shield relative to said syringe barrel.

34. A medical device for delivering a medicament to a patient, comprising:
  a syringe assembly comprising:
    a barrel having a forward end and a rear end and defining a reservoir within which the medicament may be contained;
    a needle cannula having a forward tip and being coupled to said forward end of said barrel and in fluid communication with said reservoir; and
    a plunger having a first end with a stopper positioned in said reservoir and a second end having a thumb pad for receiving medicament delivery pressure for causing said plunger to move within said reservoir to cause the medicament to be expelled from said reservoir;
  a shield releasably mounted on a front portion of said barrel at a first position, wherein one of said shield and said barrel defines two track arrangements on opposing sides of said one of said shield and said barrel, each of said track arrangements having an entry track having an end joined to a lockout track at an intersection, a first portion of said lockout track extending beyond said intersection to a first end of said lockout track and a second portion of said lockout track extending beyond said intersection to a second end of said lockout track, and the other of said shield and said barrel includes radial projections arranged on resilient lever arms and guidably inserted in respective ones of said track arrangements;

means for urging said shield in a forward direction relative to said syringe assembly;

means for retaining said shield in said first position;

means for allowing movement of said shield from said first position to a second position by interaction with a patient's skin and against the urgency of said urging member when said needle cannula is inserted into a patient for delivery of the medicament, wherein, in each of said track arrangements, said radial projection moving from a first projection position along said entry track at least to the intersection and into a second projection position in said lock-out track during movement of said shield from the first position to the second position; and means for allowing movement of said shield from said second position to a third position by the urgency of said means for urging upon removal of said needle cannula from said patient, wherein said forward tip of said needle cannula is covered by said shield when said shield is in said third position, wherein, in each of said track arrangements, said radial projection moving in said lock-out track from said second projection position to a third projection position solely by the urgency of said urging member during movement of said shield from the second position to the third position, the forward ends of said lockout tracks being axially offset so that said shield is held askew relative to said needle cannula by the urgency of said urging member when said shield is in the third position, and wherein said one of said shield and said barrel further comprises a blocking element arranged at said end of said entry track proximate said intersection of at least one of said track arrangements, said blocking element having a fixed blocking surface facing said lock-out track of said at least one of said track arrangements and blocking reentry of the associated one of said pins into said entry track from said lock-out track.

35. The medical device of claim 34, further comprising means for preventing said shield from moving back to said first position after said shield is moved to said second position, wherein, in each of said track arrangements, said third pin position is at one of the ends of said lock-out track, and said pin is movable from said second pin position to the other one of the ends of said lock-out track after said pin enters said lock-out track at said second position, whereby said means for preventing prevents said pin from entering said entry track before said shield reaches a rearmost position of said shield relative to said syringe assembly.

\* \* \* \* \*